United States Patent
Venturino et al.

(10) Patent No.: US 7,682,554 B2
(45) Date of Patent: Mar. 23, 2010

(54) METHOD AND APPARATUS TO MECHANICALLY SHAPE A COMPOSITE STRUCTURE

(75) Inventors: Michael B. Venturino, Appleton, WI (US); Seth M. Newlin, Paris, TX (US); Paul E. Olmstead, Menasha, WI (US); Susan J. Daniels, Neenah, WI (US); Sara J. Schewe, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1240 days.

(21) Appl. No.: 11/215,864

(22) Filed: Aug. 30, 2005

(65) Prior Publication Data

US 2007/0045905 A1    Mar. 1, 2007

(51) Int. Cl.
- B29C 47/00 (2006.01)
- D04H 1/00 (2006.01)
- D04H 3/02 (2006.01)
- D01D 5/092 (2006.01)

(52) U.S. Cl. .............. 264/555; 264/518; 264/103; 264/115; 264/121; 264/167; 264/309; 425/81.1; 425/83.1; 425/72.2

(58) Field of Classification Search .......... 264/103, 264/115, 555, 121, 167, 309; 425/81.1, 83.1, 425/72.2
See application file for complete search history.

(56) References Cited

U.S. PATENT DOCUMENTS

| | | | |
|---|---|---|---|
| 2,430,868 A * | 11/1947 | Francis, Jr. .......... 264/115 |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,527,221 A | 9/1970 | Croon |
| 3,532,014 A | 10/1970 | Frankz |
| 3,542,615 A | 11/1970 | Dobo et al. |
| 3,559,648 A | 2/1971 | Mason, Jr. |
| 3,692,618 A | 9/1972 | Dorschner et al. |
| 3,802,817 A | 4/1974 | Matsuki et al. |
| 3,848,598 A | 11/1974 | Mesek |
| 3,849,241 A | 11/1974 | Butin et al. |
| 3,851,356 A | 12/1974 | Savich |
| 3,957,186 A | 5/1976 | Babcock |
| 3,973,291 A | 8/1976 | Kolbach |
| 3,975,222 A | 8/1976 | Mesek |

(Continued)

FOREIGN PATENT DOCUMENTS

DE    195 30 771 A1    2/1997

(Continued)

*Primary Examiner*—Joseph S Del Sole
*Assistant Examiner*—Nahida Sultana
(74) *Attorney, Agent, or Firm*—David J. Arteman; Bryan R. Rosiejka

(57) ABSTRACT

An apparatus for forming a shaped fibrous nonwoven structure including a delivery system adapted to provide a high speed composite stream comprising thermoplastic polymer fibers and a secondary material. The apparatus also includes a movable collection device having a collection surface which intersects the composite stream, and at least one deflector to mechanically redirect at least a portion of the composite stream. Further the deflector moves in synchronization with the movable collection device, such that the composite stream is collected on the collection surface forming a fibrous nonwoven structure having at least one non-linear edge.

20 Claims, 5 Drawing Sheets

U.S. PATENT DOCUMENTS

| | | | |
|---|---|---|---|
| 3,994,047 A | 11/1976 | Lee et al. | |
| 3,996,825 A | 12/1976 | Terry | |
| 4,016,628 A | 4/1977 | Kolbach | |
| 4,100,324 A * | 7/1978 | Anderson et al. | 442/344 |
| 4,216,687 A | 8/1980 | Passafiume et al. | |
| 4,279,369 A | 7/1981 | Passafiume | |
| 4,340,563 A | 7/1982 | Appel et al. | |
| 4,349,140 A | 9/1982 | Passafiume | |
| 4,353,491 A | 10/1982 | Passafiume | |
| 4,388,056 A | 6/1983 | Lee et al. | |
| 4,425,127 A | 1/1984 | Suzuki et al. | |
| 4,441,935 A | 4/1984 | Middel et al. | |
| 4,495,119 A | 1/1985 | Chung | |
| 4,557,777 A | 12/1985 | Sabee | |
| 4,567,796 A | 2/1986 | Kloehn et al. | |
| 4,573,382 A | 3/1986 | Kloehn et al. | |
| 4,592,708 A | 6/1986 | Feist et al. | |
| 4,666,647 A | 5/1987 | Enloe et al. | |
| 4,674,966 A | 6/1987 | Johnson et al. | |
| 4,675,144 A | 6/1987 | Hammond | |
| 4,685,915 A | 8/1987 | Hasse et al. | |
| 4,690,716 A | 9/1987 | Sabol et al. | |
| 4,690,853 A | 9/1987 | Hammond | |
| 4,760,764 A | 8/1988 | De Jonckheere et al. | |
| 4,761,258 A | 8/1988 | Enloe | |
| 4,859,388 A | 8/1989 | Peterson et al. | |
| 4,892,470 A | 1/1990 | Farrington et al. | |
| 4,904,439 A * | 2/1990 | Farrington et al. | 264/510 |
| 4,904,440 A | 2/1990 | Angstadt | |
| 4,905,340 A * | 3/1990 | Gutschmit | 15/316.1 |
| 4,915,897 A | 4/1990 | Farrington et al. | |
| 4,921,659 A * | 5/1990 | Marshall et al. | 264/510 |
| 4,966,059 A | 10/1990 | Landeck | |
| 4,971,852 A | 11/1990 | Hammond | |
| 5,004,579 A | 4/1991 | Wislinski et al. | |
| 5,079,774 A * | 1/1992 | Mendez et al. | 372/27 |
| 5,145,351 A | 9/1992 | Rossi | |
| 5,213,881 A | 5/1993 | Timmons et al. | |
| 5,226,991 A | 7/1993 | Svaighert | |
| 5,288,220 A | 2/1994 | Kugler et al. | |
| 5,306,453 A * | 4/1994 | Shulman | 264/121 |
| 5,447,677 A | 9/1995 | Griffoul et al. | |
| 5,479,696 A | 1/1996 | McNneil | |
| 5,514,104 A | 5/1996 | Cole et al. | |
| 5,540,872 A | 7/1996 | Ulman | |
| 5,597,437 A | 1/1997 | Lange et al. | |
| 5,651,778 A | 7/1997 | Melius et al. | |
| 5,665,300 A | 9/1997 | Brignola et al. | |
| 5,665,396 A | 9/1997 | Ulman | |
| 5,695,846 A | 12/1997 | Lange et al. | |
| 5,756,039 A | 5/1998 | Mcfall et al. | |
| 5,772,813 A | 6/1998 | Bitowft et al. | |
| 5,846,232 A | 12/1998 | Serbiak et al. | |
| 5,866,173 A | 2/1999 | Reiter et al. | |
| 5,983,457 A | 11/1999 | Toney et al. | |
| 6,066,775 A | 5/2000 | Bachar | |
| 6,096,247 A | 8/2000 | Ulsh et al. | |
| 6,098,249 A | 8/2000 | Toney et al. | |
| 6,330,735 B1 | 12/2001 | Hahn et al. | |
| 6,485,477 B2 | 11/2002 | Widlund | |
| 6,485,667 B1 * | 11/2002 | Tan | 264/510 |
| 6,604,926 B2 | 8/2003 | Geisen et al. | |
| 6,627,130 B2 | 9/2003 | Kugler et al. | |
| 6,630,088 B1 | 10/2003 | Venturino et al. | |
| 6,630,096 B2 | 10/2003 | Venturino et al. | |
| 6,632,209 B1 | 10/2003 | Chmielewski | |
| 6,732,868 B2 * | 5/2004 | Takagaki et al. | 210/490 |
| 6,818,166 B2 | 11/2004 | Edwardson et al. | |
| 6,846,448 B2 | 1/2005 | Rymer et al. | |
| 6,989,125 B2 * | 1/2006 | Boney et al. | 264/465 |
| 7,470,389 B2 * | 12/2008 | Berrigan et al. | 264/555 |
| 7,476,350 B2 * | 1/2009 | Allen | 264/40.1 |
| 2001/0003151 A1 | 6/2001 | Wallström | |
| 2003/0114814 A1 | 6/2003 | Baker et al. | |
| 2003/0149419 A1* | 8/2003 | Gibbs | 604/386 |
| 2003/0236510 A1 | 12/2003 | Yasumura et al. | |
| 2004/0023583 A1 | 2/2004 | Venturino et al. | |
| 2004/0116885 A1 | 6/2004 | Soerens et al. | |
| 2004/0119208 A1* | 6/2004 | Gray et al. | 264/504 |
| 2004/0211711 A1* | 10/2004 | Palmer | 209/635 |
| 2005/0082723 A1 | 4/2005 | Brock et al. | 264/439 |
| 2005/0087287 A1* | 4/2005 | Lennon et al. | 156/167 |
| 2005/0087288 A1* | 4/2005 | Haynes et al. | 156/167 |
| 2005/0109442 A1 | 5/2005 | Neubauer et al. | |
| 2005/0113791 A1 | 5/2005 | Neubauer et al. | |
| 2005/0129793 A1* | 6/2005 | Choi | 425/72.2 |
| 2005/0140067 A1* | 6/2005 | Berrigan et al. | 264/518 |
| 2007/0001333 A1 | 1/2007 | Dias et al. | |

FOREIGN PATENT DOCUMENTS

| | | |
|---|---|---|
| EP | 0 308 911 A2 | 3/1989 |
| EP | 0 383 616 A1 | 8/1990 |
| EP | 0 396 094 A2 | 11/1990 |
| EP | 0 478 182 B1 | 1/1995 |
| EP | 0 479 442 B1 | 6/1997 |
| EP | 1 240 933 A2 | 9/2002 |
| EP | 1 371 348 A2 | 12/2003 |
| EP | 1 457 185 A1 | 9/2004 |
| WO | WO 03/051253 A1 | 6/2003 |
| WO | WO 2005/040477 A1 | 5/2005 |

* cited by examiner

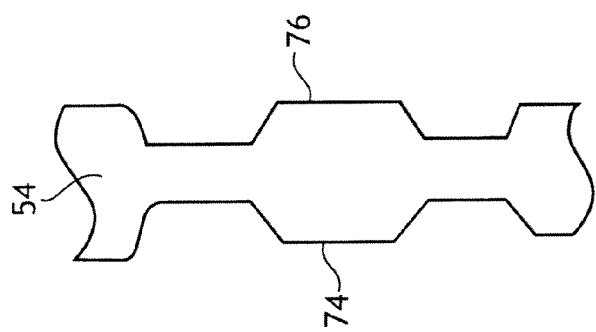
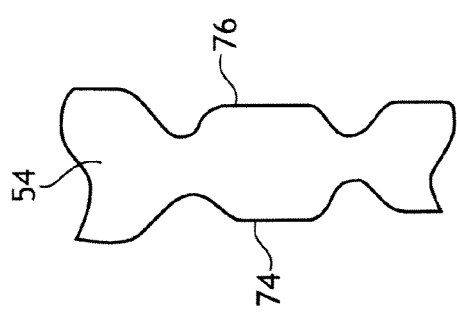
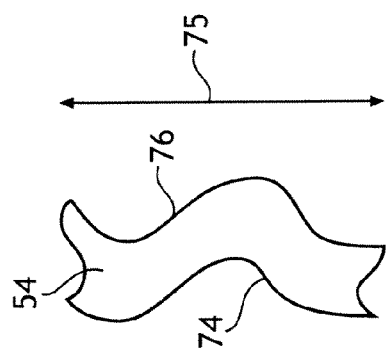
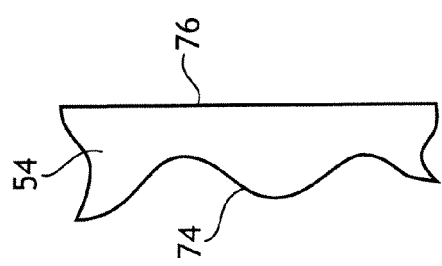
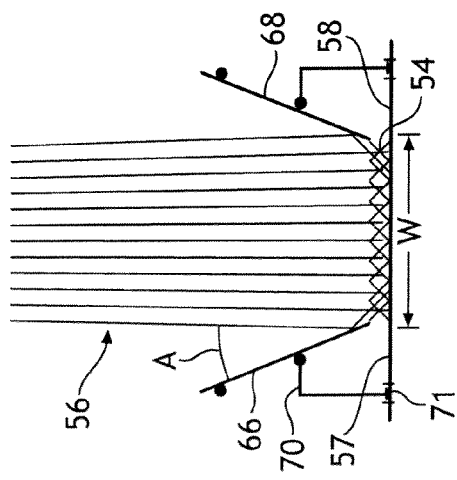
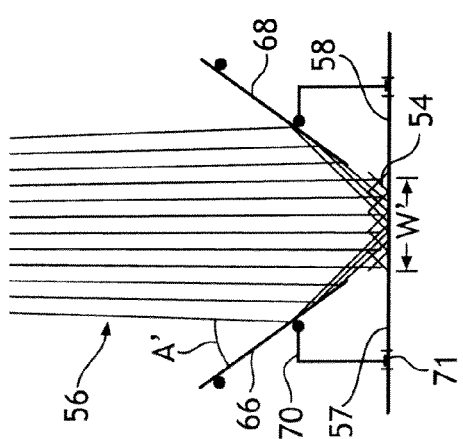

METHOD AND APPARATUS TO MECHANICALLY SHAPE A COMPOSITE STRUCTURE

BACKGROUND

Disposable absorbent articles are used for a variety of applications including disposable diapers, training pants, disposable swim pants, adult incontinence garments, feminine hygiene products, wound dressings, nursing pads, bed pads, wipes, bibs, wound dressings, surgical capes or drapes, and the like. Such disposable absorbent products are generally suited to absorb many substances such as water and body exudates such as urine, menses, blood, and the like.

Some disposable absorbent articles include absorbent structures formed from densified cellulose intermixed with superabsorbent particles. Other absorbent structures are formed from high integrity absorbent structures containing high concentrations of superabsorbent particles entangled or otherwise commingled with long thermoplastic fibers and/or cellulosic fibers (composite nonwoven structures) to improve fit, comfort, and/or performance. These composite nonwoven structures may be expensive due to the addition of thermoplastic fibers. Additionally, these composite nonwoven structures may not be conducive to shaping using conventions methods such as die cutting because of the difficulties in utilizing the portions removed. Conventional methods, such as vacuum forming have not been suitable for forming shaped absorbent structures.

Therefore, there exists a need for apparatus and methods to shape high speed composite streams to form composite nonwoven structures.

SUMMARY OF THE INVENTION

In response to the foregoing need, the present inventor undertook intensive research and development efforts that resulted in the discovery of a method for producing fibrous nonwoven structures. One version of the present invention includes an apparatus for forming a shaped fibrous nonwoven structure including a delivery system adapted to provide a high speed composite stream comprising thermoplastic polymer fibers and a secondary material. The apparatus also includes a movable collection device having a collection surface which intersects the composite stream, and at least one deflector to mechanically redirect at least a portion of the composite stream. Further the deflector moves in synchronization with the movable collection device, such that the composite stream is collected on the collection surface forming a fibrous nonwoven structure having at least one non-linear edge.

Another version of the present invention provides a method for forming a shaped fibrous nonwoven structure including delivering a high speed composite stream including thermoplastic polymer fibers and a secondary material. The method also includes mechanically redirecting at least a portion of the composite stream with a deflector and collecting the composite stream on a collection surface of a movable collection device. Further, the deflector moves in synchronization with the movable collection device, such that the composite stream is collected on the collection surface forming a fibrous nonwoven structure having at least one non-linear edge.

Still another version of the present invention includes a method for forming a shaped fibrous nonwoven structure including delivering a high speed composite stream including thermoplastic polymer fibers and a secondary material at a velocity of at least 50 feet/sec (15 m/sec). The method also includes mechanically redirecting at least a portion of the composite stream with a deflector and collecting the composite stream on a collection surface of a movable collection device. Further, the deflector is fixedly attached to the movable collection device, such that the composite stream is collected on the collection surface forming a fibrous nonwoven structure having at least one non-linear edge, and the high speed composite stream comprises from about 5-25% by weight cellulose fibers, from about 40-90% superabsorbent particles and about 5-55% thermoplastic polymer fibers.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 3 is an illustration of an apparatus which may be used to form a shaped composite nonwoven composite structure with deflectors in a first position.

FIG. 4 is an illustration of the apparatus of FIG. 3 with deflectors in a second position.

FIGS. 5A-D are illustrations of four shaped composite nonwoven structures

DETAILED DESCRIPTION

Definitions

Figure 1:
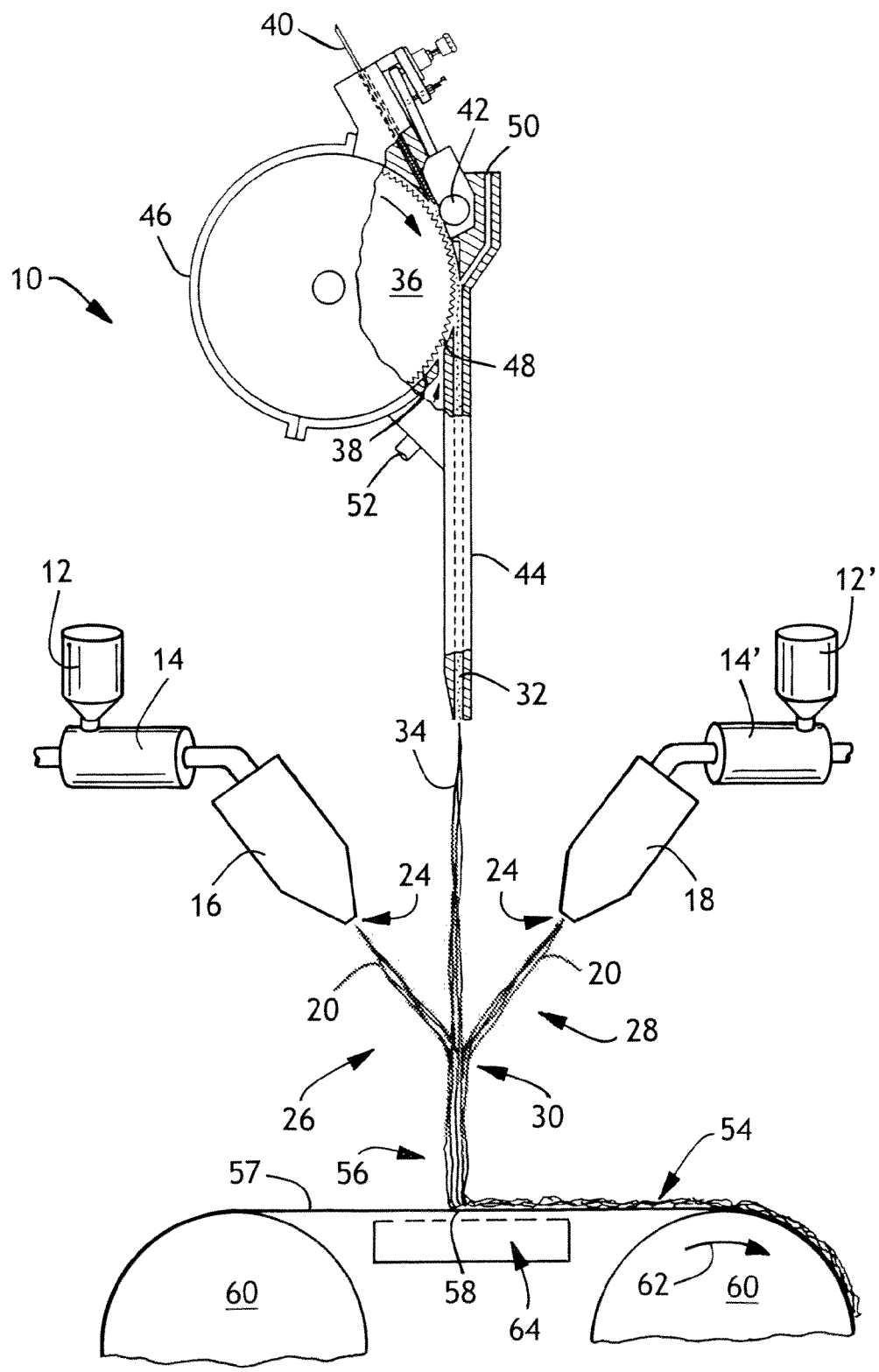
FIG. 1 is an illustration of an apparatus which may be used to form a composite nonwoven composite structure.

The term "absorbent material" refers to materials such as cellulose fibers which are capable of absorbing at least five times but generally less than 15 times their own weight of an aqueous solution containing 0.9% by weight sodium chloride. Absorbent material under the most favorable conditions can also include synthetic fiber matrices such as spunbond, meltblown and bonded carded webs, and the like.

The term "superabsorbent material" refers to water-swellable organic and inorganic materials that are capable of absorbing at least 15 times their own weight in a solution of 0.9% by weight aqueous sodium chloride under the most favorable conditions.

The term "cutting" refers to any method used to trim or cut the lateral side edges of an absorbent core, to form the absorbent core into a desired shape, typically a shape other than a pre-formed rectangle. Cutting processes include without limitation die cutting, water cutting, laser cutting, sawing and the like.

The term "substantially perpendicular" means within about 15 degrees of perpendicular. Where "perpendicular" is defined by a 90-degree angle relative to a direction, "substantially perpendicular" refers to an angle of about (75)-(105) degrees.

The term "substantially parallel" means within about 15 degrees of parallel. Where "parallel" is defined by a 0-degree angle relative to a direction, "substantially parallel" refers to an angle of about (−15)-(15) degrees.

The term "hydrophilic" describes fibers or the surfaces of fibers and other materials which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system.

When measured with this system, fibers having contact angles less than 90° are designated "wettable" or hydrophilic, and fibers having contact angles greater than 90° are designated "nonwettable" or hydrophobic.

The term "meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al.

Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons et al.

Meltblown fibers may be continuous or discontinuous and are generally self bonding when deposited onto a collecting surface. Meltblown fibers used in the present invention are suitably substantially continuous in length.

The term "nonwoven" as used in reference to a material, web or fabric refers to such a material, web or fabric having a structure of individual fibers or threads that are interlaid, but not in a regular or identifiable manner as in a knitted fabric. Nonwoven materials, fabrics or webs have been formed from many processes such as, for example, meltblowing processes, spunbonding processes, air laying processes, and bonded carded web processes. The basis weight of nonwovens is usually expressed in ounces of material per square yard (osy) or grams per square meter (gsm) and the fiber diameters are usually expressed in microns. (Note that to convert from osy to gsm, multiply osy by 33.91.)

The term "spunbond fibers" means small diameter fibers that are typically formed by extruding molten thermoplastic material as filaments from a plurality of fine usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

The terms "particle," "particles," "particulate," "particulates" and the like refer to superabsorbent material generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers are also contemplated for inclusion herein. The terms "particle" or "particulate" may also include an agglomeration comprising more than one individual particle, particulate or the like. Additionally, a particle, particulate or any desired agglomeration thereof may be composed of more than one type of material. For instance, superabsorbent particles commonly include a core, shell, crosslinking agent, anti-dust treatment, etc., and may include one or more superabsorbent polymers.

The term "stretchable" refers to materials which, upon application of a stretching force, can be extended to a stretched dimension which is at least 150% of an original dimension (i.e., at least 50% greater than an original, unstretched dimension) in one or more directions without rupturing. The term "elastic" refers to materials which are stretchable and which, upon release of the stretching force, will retract (recover) by at least 50% of the difference between the stretched dimension and the original dimension. For instance, a material having an original dimension of 20 cm is stretchable if it can be extended to a dimension of at least 30 cm without rupture. The same material is elastic if, after being extended to 30 cm, it retracts to a dimension of 25 cm or less when the stretching force is removed.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Turning now to the figures wherein like reference numerals represent the same or equivalent structure and, in particular, to FIG. 1 where it can be seen that an exemplary apparatus for forming a fibrous nonwoven composite structure is generally represented by reference numeral 10. In forming the fibrous nonwoven composite structure, pellets or chips, etc. (not shown) of a thermoplastic polymer are introduced into a pellet hopper 12 of an extruder 14. The thermoplastic polymer may include any polymer capable of being formed into fibers.

The thermoplastic polymer may include polymers which form stretchable or elastic fibers. Polymers which may form stretchable fibers include KRATON® elastomers, HYTREL® elastomers, ESTANE® elastomeric polyurethanes (available from B.F. Goodrich and Company located in Cleveland, Ohio), PEBAX® elastomers, and elastomeric polyolefins such as VISTAMAXX® (available from Exxon Mobil Corporation of Irving, Tex.), AFFINITY® (available from Dow Chemical of Midland, Mich.), and the like.

The extruder 14 has an extrusion screw (not shown) which is driven by a conventional drive motor (not shown). As the polymer advances through the extruder 14, due to rotation of the extrusion screw by the drive motor, it is progressively heated to a molten state. Heating the thermoplastic polymer to the molten state may be accomplished in a plurality of discrete steps with its temperature being gradually elevated as it advances through discrete heating zones of the extruder 14 toward two meltblowing dies 16 and 18, respectively. The meltblowing dies 16 and 18 may be yet another heating zone where the temperature of the thermoplastic polymer is maintained at an elevated level for extrusion.

Each meltblowing die is configured so that two streams of attenuating gas per die converge to form a single stream of gas which entrains and attenuates molten threads 20, as the threads 20 exit small holes or orifices 24 in the meltblowing die. The molten threads 20 are attenuated into fibers or, depending upon the degree of attenuation, microfibers, of a small diameter, which is usually less than the diameter of the orifices 24. Thus, each meltblowing die 16 and 18 has a corresponding single stream of gas 26 and 28 containing entrained and attenuated polymer fibers. The gas streams 26 and 28 containing polymer fibers are aligned to converge at an impingement zone 30.

One or more types of secondary materials, for example fibers and/or particulates are added to the two streams 26 and 28 of thermoplastic polymer fibers or microfibers 24 at the impingement zone 30. Introduction of secondary fibers 32 into the two streams 26 and 28 of thermoplastic polymer fibers 24 may be designed to produce a graduated distribution of secondary fibers 32 within the combined streams 26 and 28 of thermoplastic polymer fibers. This may be accomplished by merging a secondary gas stream 34 containing the secondary fibers 32 between the two streams 26 and 28 of thermoplastic polymer fibers 24 so that all three gas streams converge in a controlled manner. Alternatively, the introduction of secondary fibers 32 into the two streams 26 and 28 of thermoplastic polymer fibers 24 is may be designed to produce a homogeneous distribution of secondary fibers 32 within the combined streams 26 and 28 of thermoplastic polymer fibers.

Apparatus for accomplishing this merger may include a conventional picker roll 36 arrangement which has a plurality of teeth 38 that are adapted to separate a mat or batt 40 of secondary fibers into the individual secondary fibers 32. The mat or batt of secondary fibers 40 which is fed to the picker roll 36 may be a sheet of pulp fibers (if a two-component mixture of thermoplastic polymer fibers and secondary pulp fibers is desired), a mat of staple fibers (if a two-component mixture of thermoplastic polymer fibers and a secondary staple fibers is desired) or both a sheet of pulp fibers and a mat of staple fibers (if a three-component mixture of thermoplastic polymer fibers, secondary staple fibers and secondary pulp fibers is desired). In embodiments where, for example, an absorbent material is desired, the secondary fibers 32 are absorbent fibers. The secondary fibers 32 may generally be selected from the group including one or more polyester fibers, polyamide fibers, cellulosic derived fibers such as, for example, rayon fibers and wood pulp fibers, multi-component fibers such as, for example, sheath-core multi-component fibers, natural fibers such as silk fibers, wool fibers or cotton fibers or electrically conductive fibers or blends of two or more of such secondary fibers. Other types of secondary fibers 32 such as, for example, polyethylene fibers and polypropylene fibers, as well as blends of two or more of other types of secondary fibers 32 may be utilized. The secondary fibers 32 may be microfibers or the secondary fibers 32 may be macrofibers having an average diameter of from about 300 microns to about 1,000 microns.

The sheets or mats 40 of secondary fibers 32 are fed to the picker roll 36 by a roller arrangement 42. After the teeth 38 of the picker roll 36 have separated the mat of secondary fibers 40 into separate secondary fibers 32 the individual secondary fibers 32 are conveyed toward the stream of thermoplastic polymer fibers or microfibers 24 through a nozzle 44. A housing 46 encloses the picker roll 36 and provides a passageway or gap 48 between the housing 46 and the surface of the teeth 38 of the picker roll 36. A gas, for example, air, is supplied to the passageway or gap 48 between the surface of the picker roll 36 and the housing 46 by way of a gas duct 52. The gas duct 52 may enter the passageway or gap 48 generally at the junction 52 of the nozzle 44 and the gap 48. The gas is supplied in sufficient quantity to serve as a medium for conveying the secondary fibers 32 through the nozzle 44. The gas supplied from the duct 52 also serves as an aid in removing the secondary fibers 32 from the teeth 38 of the picker roll 36. The gas may be supplied by any conventional arrangement such as, for example, an air blower (not shown). It is contemplated that additives and/or other materials may be added to or entrained in the gas stream to treat the secondary fibers.

Generally speaking, the individual secondary fibers 32 are conveyed through the nozzle 44 at about the velocity at which the secondary fibers 32 leave the teeth 38 of the picker roll 36. In other words, the secondary fibers 32, upon leaving the teeth 38 of the picker roll 36 and entering the nozzle 44 generally maintain their velocity in both magnitude and direction from the point where they left the teeth 38 of the picker roll 36. Such an arrangement, which is discussed in more detail in U.S. Pat. No. 4,100,324 to Anderson, et al., hereby incorporated by reference, aids in substantially reducing fiber floccing.

The width of the nozzle 44 should be aligned in a direction generally parallel to the width of the meltblowing dies 16 and 18. Desirably, the width of the nozzle 44 should be about the same as the width of the meltblowing dies 16 and 18. Usually, the width of the nozzle 44 should not exceed the width of the sheets or mats 40 that are being fed to the picker roll 36. Generally speaking, it is desirable for the length of the nozzle 44 to be as short as equipment design will allow.

The picker roll 36 may be replaced by a conventional particulate injection system to form a composite nonwoven structure 54 containing various secondary particulates. A combination of both secondary particulates and secondary fibers could be added to the thermoplastic polymer fibers prior to formation of the composite nonwoven structure 54 if a conventional particulate injection system was added to the system illustrated in FIG. 1 at 50. The particulates may be, for example, charcoal, clay, starches, and/or hydrocolloid (hydrogel) particulates commonly referred to as super-absorbents.

FIG. 1 further illustrates that the secondary gas stream 34 carrying the secondary fibers 32 is directed between the streams 26 and 28 of thermoplastic polymer fibers so that the streams contact at the impingement zone 30. The velocity of the secondary gas stream 34 may be adjusted so that it is greater than the velocity of each stream 26 and 28 of thermoplastic polymer fibers 24 when the streams contact at the impingement zone 30. Alternatively, the velocity of the secondary gas stream 34 may be adjusted so that it is less than the velocity of each stream 26 and 28 of thermoplastic polymer fibers 24 when the streams contact at the impingement zone 30. The velocity of the secondary gas stream 34 may be greater than 500 ft/sec, alternatively greater than 1000 ft/sec, alternatively greater than 5000 ft/sec, and finally alternatively greater than 10,000 ft/sec.

The velocity difference between the gas streams may be such that the secondary fibers 32 are integrated into the streams of thermoplastic polymer fibers 26 and 28 in such manner that the secondary fibers 32 become gradually and only partially distributed within the thermoplastic polymer fibers 24. Generally, for increased production rates the gas streams which entrain and attenuate the thermoplastic polymer fibers 24 should have a comparatively high initial velocity, for example, from about 200 feet to over 5,000 feet per second. However, the velocity of those gas streams decreases rapidly as they expand and become separated from the meltblowing die. Thus, the velocity of those gas streams at the impingement zone may be controlled by adjusting the distance between the meltblowing die and the impingement zone. The stream of gas 34 which carries the secondary fibers 32 may have a low initial velocity when compared to the gas streams 26 and 28 which carry the meltblown fibers. Alternatively, by adjusting the distance from the nozzle 44 to the impingement zone 30 (and the distances that the meltblown fiber gas streams 26 and 28 must travel), the velocity of the gas stream 34 can be controlled to be greater than the meltblown fiber gas streams 26 and 28.

Due to the fact that the thermoplastic polymer fibers 24 are usually still semi-molten and tacky at the time of incorporation of the secondary fibers 32 into the thermoplastic polymer fiber streams 26 and 28, the secondary fibers 32 are usually not only mechanically entangled within the matrix formed by the thermoplastic polymer fibers 24 but are also thermally bonded or joined to the thermoplastic polymer fibers 24.

The delivery system provides a composite stream 56 having a velocity of greater than 200 ft/min, alternatively greater than 500 ft/min, alternatively greater than 3000 ft/min, alternatively greater than 5000 ft/sec, and finally alternatively greater than 10,000 ft/sec. For purposes of this application, a composite stream is considered a "high speed composite stream" when it has a maximum velocity of at least 200 ft/min.

The composite stream 56 may contain 0-90% absorbent fibers, alternatively 1-50% absorbent fibers, alternatively 5-25% absorbent fibers. The composite stream 56 may contain 0-99% super absorbent particles, alternatively 30-99% super absorbent particles, alternatively 40-90% super absorbent particles. The composite stream 56 may contain 1-99% thermoplastic polymer fibers, alternatively 5-90% thermoplastic polymer fibers, alternatively 5-50% thermoplastic polymer fibers.

In order to convert the composite stream 56 of thermoplastic polymer fibers 24 and secondary fibers 32 into a composite nonwoven structure 54 composed of a coherent matrix of the thermoplastic polymer fibers 24 having the secondary fibers 32 distributed therein, a movable collection device is located in the path of the composite stream 56. The movable collection device may be an endless belt 58 conventionally driven by rollers 60 and which is rotating as indicated by the arrow 62 in FIG. 1. Other collection devices are well known to those of skill in the art and may be utilized in place of the endless belt 58. For example, a porous rotating drum arrangement could be utilized. The composite stream 56 is collected as a coherent matrix of fibers on a collection surface 57 of the endless belt 58 to form the composite nonwoven web 54. Vacuum boxes 64 assist in retention of the matrix on the collection surface 57. The vacuum may be set at about 1 to about 4 inches of water column. The composite stream 56 may be positioned at a 90 degree angle to the movement of the collection surface 57 (as illustrated), such that a 10 inch wide composite stream would produce a 10 inch wide composite nonwoven web 54. Alternatively, the composite stream may be positioned at an angle different than 90 degrees such that a 10 inch wide composite stream would produce a composite nonwoven web 54 of less then 10 inches wide.

The composite structure 54 is coherent and may be removed from the belt 58 as a self-supporting nonwoven material. Generally speaking, the composite structure has adequate strength and integrity to be used without any post-treatments such as pattern bonding and the like. If desired, a pair of pinch rollers or pattern bonding rollers may be used to bond portions of the material. Although such treatment may improve the integrity of the composite structure 54 it also tends to compress and densify the structure.

Figure 2:
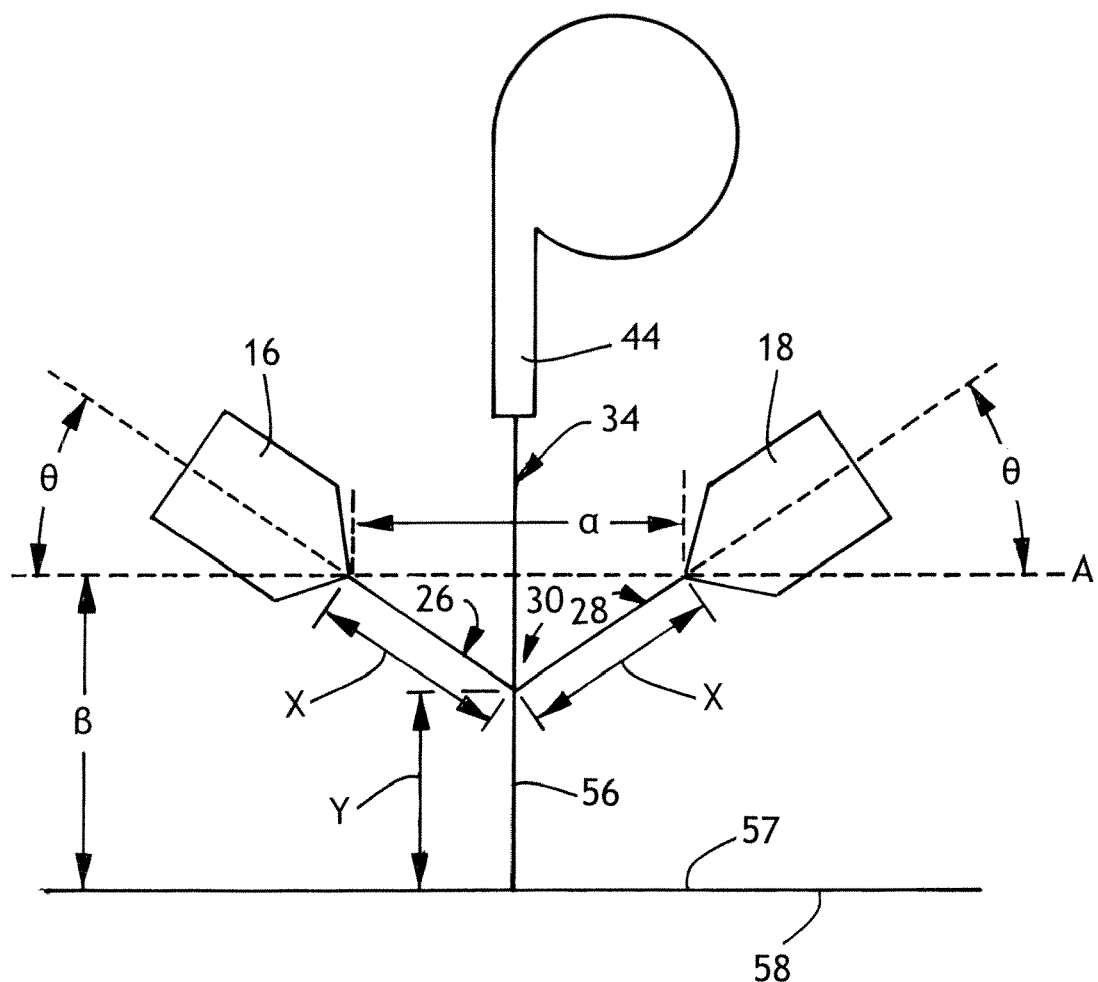
FIG. 2 is an illustration of certain features of the apparatus shown in FIG. 1.

Referring now to FIG. 2 of the drawings, there is shown a schematic diagram of an exemplary process described in FIG. 1. FIG. 2 highlights process variables which will affect the type of composite nonwoven structure made. Also shown are various forming distances which affect the type of composite nonwoven composite structure.

The melt-blowing die arrangements 16 and 18 are mounted so they each can be set at an angle. The angle is measured from a plane tangent to the two dies (plane A). Generally speaking, plane A is parallel to the collection surface 57. Typically, each die is set at an angle ($\theta$) and mounted so that the streams of gas-borne fibers and microfibers 26 and 28 produced from the dies intersect in a zone below plane A (i.e., the impingement zone 30).

Desirably, angle $\theta$ may range from about 30 to about 75 degrees. More desirably, angle $\theta$ may range from about 35 to about 60 degrees. Even more desirably, angle $\theta$ may range from about 45 to about 55 degrees.

Meltblowing die arrangements 16 and 18 are separated by a distance ($\alpha$). Generally speaking, distance $\alpha$ may range up to about 16 inches. Distance $\alpha$ may be set even greater than 16 inches to produce a lofty, bulky material which is somewhat weaker and less coherent than materials produced at shorter distances. Desirably, $\alpha$ may range from about 5 inches to about 10 inches. More desirably, a may range from about 6.5 to about 9 inches. Importantly, the distance $\alpha$ between the meltblowing dies and the angle $\theta$ of each meltblowing die determines location of the impingement zone 30.

The distance from the impingement zone 30 to the tip of each meltblowing die (i.e., distance X) should be set to minimize dispersion of each stream of fibers and microfibers 26 and 28. For example, this distance may range from about 0 to about 16 inches. Desirably, this distance should be greater than 2.5 inches. For example, from about 2.5 to 6 inches the distance from the tip of each meltblowing die arrangement can be determined from the separation between the die tips ($\alpha$) and the die angle ($\theta$) utilizing the formula: $X=\alpha/(2 \cos \theta)$ Generally speaking, the dispersion of the composite stream 56 may be minimized by selecting a proper vertical forming distance (i.e., distance $\beta$) before the stream 56 contacts the forming surface 58. $\beta$ is the distance from the meltblowing die tips to the forming surface 58. A shorter vertical forming distance is generally desirable for minimizing dispersion. This must be balanced by the need for the extruded fibers to solidify from their tacky, semi-molten state before contacting the forming surface 58. For example, the vertical forming distance (β) may range from about 3 to about 15 inches from the meltblown die tip. The vertical forming distance (β.) may be set even greater than 15 inches to produce a lofty, bulky material which is somewhat weaker and less coherent than materials produced at shorter distances. Desirably, this vertical distance (β) may be about 7 to about 11 inches from the die tip.

An important component of the vertical forming distance β is the distance between the impingement zone 30 and the forming surface 58 (i.e., distance Y). The impingement zone 30 should be located so that the integrated streams have only a minimum distance (Y) to travel to reach the forming surface 58 to minimize dispersion of the entrained fibers and microfibers. For example, the distance (Y) from the impingement zone to the forming surface may range from about 0 to about 12 inches. Desirably, the distance (Y) from the impingement point to the forming surface may range from about 3 to about 7 inches. The distance from the impingement zone 30 and the forming surface 58 can be determined from the vertical forming distance (β), the separation between the die tips (60) and the die angle (θ) utilizing the formula:

$$Y=\beta-((\alpha/2)*\cos\theta)$$

Gas entrained secondary fibers are introduced into the impingement zone via a stream 34 emanating from a nozzle 44. Generally speaking, the nozzle 44 is positioned so that its vertical axis is substantially perpendicular to plane A (i.e., the plane tangent to the meltblowing dies 16 and 18).

In some situations, it may be desirable to cool the secondary air stream 34. Cooling the secondary air stream could accelerate the quenching of the molten or tacky meltblown fibers and provide for shorter distances between the meltblowing die tip and the forming surface which could be used to minimize fiber dispersion and enhance the gradient distribution of the composite structure. For example, the temperature of the secondary air stream 34 may be cooled to about 15 to about 85 degrees Fahrenheit.

By balancing the streams of meltblown fibers 26 and 28 and secondary air stream 34, the desired die angles (θ) of the meltblowing dies, the vertical forming distance (β), the distance between the meltblowing die tips (α), the distance between the impingement zone and the meltblowing die tips (X) and the distance between the impingement zone and the forming surface (Y), it is possible to provide a controlled integration of secondary fibers within the meltblown fiber streams to produce a composite nonwoven structure having a greater concentration of meltblown fibers adjacent its exterior surfaces and a lower concentration of meltblown fibers (i.e., a greater concentration of secondary fibers and/or particulates) in the inner portion of the composite nonwoven structure.

FIGS. 3 and 4 illustrate an apparatus which may be used to form a shaped composite nonwoven structure from the composite stream 56. The apparatus may include a single deflector, two deflectors or more than two deflectors. Specifically illustrated are a first deflector 66 and a second deflector 68 which mechanically redirect first and second portions of the composite stream 56. At least one deflector is movable in synchronization with the moveable collection device such that varying portions of the collection surface 57 are exposed to the composite stream 56. Alternatively, the first and second deflectors 66, 68 may both move in synchronization with the moveable collection device (as show an endless belt 58). The deflectors 66, 68 move in response to the movement of the collection device, this synchronization allows the edges of the composite nonwoven structure 54 to be non-linear as the shape of the edges are determine by the specific synchronization between the deflectors 66, 68 and the collection device.

Apparatus using only vacuum to modify composite stream 56 may be unsuccessful at redirecting high speed composite streams 56. The kinetic energy contained in a composite stream 56 moving a high speed is very difficult to overcome with the relatively weak forces that can be achieved with vacuum. For this reason, a deflector which mechanically redirects the stream may provide a benefit. For purposes of this application, mechanical redirection of a stream means to use a physical barrier which intersects and changes the direction of a stream.

The movement of the deflectors 66, 68 may be controlled electronically, such that the position or movement of the endless belt 58 is detected creating a signal, that signal may then be fed into a controller which then signals for the deflectors 66, 68 to be moved. Alternatively, the deflectors 66, 68 may be controlled mechanically. The collection device may contain a grove 71 which the deflectors 66, 68 are slideably attached to. Alternatively, the collection device may drive a geared mechanism or cam which is then connected to the deflector 66, 68 which move the deflectors 66, 68.

As shown in FIGS. 3 and 4, the first deflector 66 is connected to a first actuator 70 which moves the first deflector 66 such that the deflector 66 redirects more or less of the composite stream 56. This movement of the first deflector 66 exposes varying portions of the collection surface 57 to the composite stream 56. The first actuator 70 slides in first groove 71. The actuator 70 may move the deflector 66 about a pivot as shown; alternatively the actuator 70 may move the deflector 66 by sliding it along a track. As shown in FIG. 3, with the actuator 70 in a first position, the first deflector 66 intersects the composite stream 56 at angle A, exposing a portion of the collection surface 57 to the composite stream 56, specifically, in conjunction with the second deflector 68, a width w of the collection surface 57 is exposed to the composite stream 56.

FIG. 4 shows the first and second deflectors 66, 68 in a second position after they have moved in synchronization with the movable collection device. The first deflector 66 intersects the composite stream 56 at angle A', exposing a portion of the collection surface 57 to the composite stream 56, specifically, in conjunction with the second deflector 68, a width w' of the collection surface 57 is exposed to the composite stream 56. Utilizing this apparatus a composite nonwoven structure with at least one non-linear edge may be produced, a shaped composite nonwoven structure, specifically a shaped composite nonwoven structure having varying widths.

The angle A that the deflector intersects the composite stream 56 may vary as illustrated in FIGS. 3 and 4. Alternatively the deflector may be constructed such that the angle A is fixed. Depending on the velocities and volume of the composite stream 56 a small angle A, A' may be more effective at deflecting the stream 56 while maintaining uniformity of the composite nonwoven structure 54. The deflector may intersect the composite stream 56 at an angle of not greater than 60 degrees, alternatively not greater than 50 degrees, alternatively not greater than 40 degrees, and finally not greater than 30 degrees.

Numerous different shapes of composite nonwoven structures may be produced. FIGS. 5A, 5B, 5C and 5D illustrate four shaped composite nonwoven structures that may be produced with the present invention. Specifically, FIG. 5A illustrates a composite nonwoven structure 54 with first 74 and second 76 edges that are asymmetric. Specifically the first edge 74 roughly corresponds to the shape of a sine wave, and the second edge 76 is roughly linear.

FIG. 5B illustrates a composite nonwoven structure 54 with first 74 and second edges 76 that are symmetric. Specifically the edges 74, 76 of the composite nonwoven structure 54 are roughly linear with roughly semi-circular indentations located periodically along the edges 74, 76. Nonwoven structures 54 with varying widths (as illustrated in FIGS. 5A, 5B and 5C) utilizing the methods and apparatus of the present invention may have a higher basis weight of material in the narrower portions than the wider portions. This feature may provide additional absorbent benefits where the narrower portions of the nonwoven structure 54 correspond to the crotch of an absorbent product.

FIG. 5C illustrates a composite nonwoven structure 54 with first 74 and second edges 76 that are symmetric. Specifically the edges 74, 76 are linear with rectilinear indentations located periodically along the edges 74, 76.

FIG. 5D illustrates a composite nonwoven structure 54 with first 74 and second edges 76 that are asymmetric. Specifically the first edge 74 roughly corresponds to the shape of a sine wave, and the second edge 76 roughly corresponds to the shape of a sine wave that is in phase with the first edge 74. FIG. 5D illustrates a shaped composite nonwoven structure 54 with a width that is uniform along it length 75.

Figure 6:
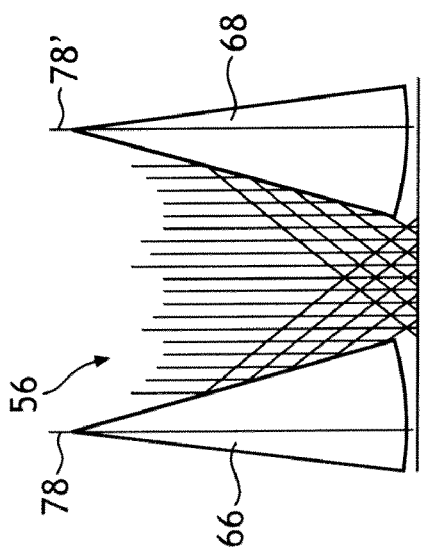
FIG. 6 is an illustration of an apparatus which may be used to form a shaped composite nonwoven structure with deflectors which rotate about an axis parallel to a path of a composite stream.
Figure 7:
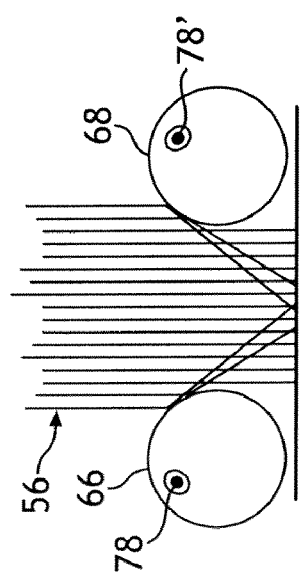
FIG. 7 is an illustration of an apparatus which may be used to form a shaped composite nonwoven structure with deflectors which rotate about an axis perpendicular to a path of a composite stream.

FIGS. 6 and 7 illustrate a second and third apparatus which may be used to form a shaped composite nonwoven structure from the composite stream 56. Specifically illustrated are a first deflector 66 and a second deflector 68 which mechanical redirects first and second portions of the composite stream 56. The first deflector 66 rotates about axis 78 and the second deflector rotates about axis 78' in synchronization with the movable collection device. As shown in FIG. 6 the axis may be substantially parallel to the composite stream and may have the shape of a cone having an off set axis. As shown in FIG. 7 the axis may be substantially perpendicular to the composite stream and may have the shape of a drum having an off set axis.

The deflectors 66, 68 may be designed such that as they rotate about their respective axes 78, 78', they mechanically redirect varying amounts of the composite stream 56. They may be designed such that the deflectors 66, 68 continuously intersect the composite stream 56, alternatively, the deflectors may intermittently intersect the composite stream 56. The deflectors 66, 68 may rotate continuously; alternately the deflectors 66, 68 may rotate intermittently in response to movement in the movable collection device.

Figure 8:
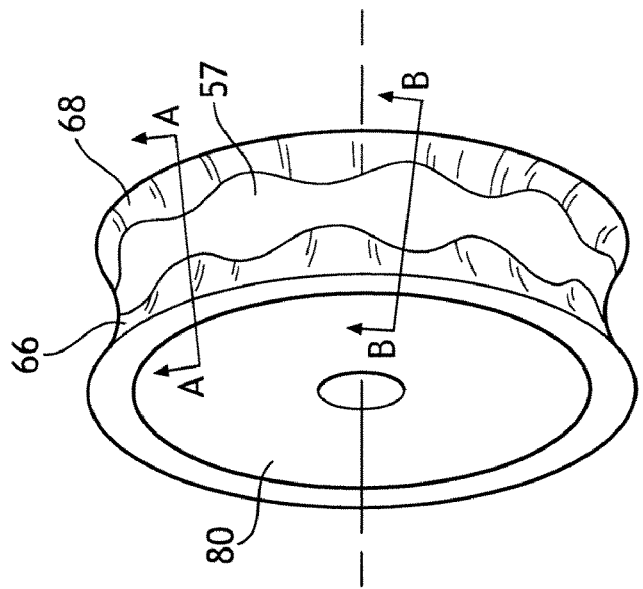
FIG. 8 is an illustration of an apparatus which may be used to form a shaped composite nonwoven structure with deflectors which are fixedly attached to a porous rotating drum.

FIG. 8 illustrates a further apparatus which may be used to form a shaped composite nonwoven structure from a composite stream 56. Specifically illustrated are a first deflector 66 and a second deflector 68 which mechanical redirect first and second portions of the composite stream 56. The first and second deflectors 66, 68 are fixedly attached to the movable collection device, as shown a porous rotating drum 80. The deflectors 66, 68 are designed such as the porous rotating drum 80 moves, the composite stream 56 is collected on the collection surface 57 in varying widths, forming a shaped composite nonwoven structure 54. The particular shape and design of the deflectors 66, 68 may vary considerably depending on the specifics of the composition of the composite stream 56 as well as the size and design of the porous rotating drum 80. The deflectors 66, 68 may be constructed of any material suitable to deflect the composite stream 56. The deflectors 66, 68 may be ridged, alternatively the deflectors 66, 68 may be flexible or deflatable to facilitate removal of the composite structure 54 from the collection surface 57.

Figure 9A:
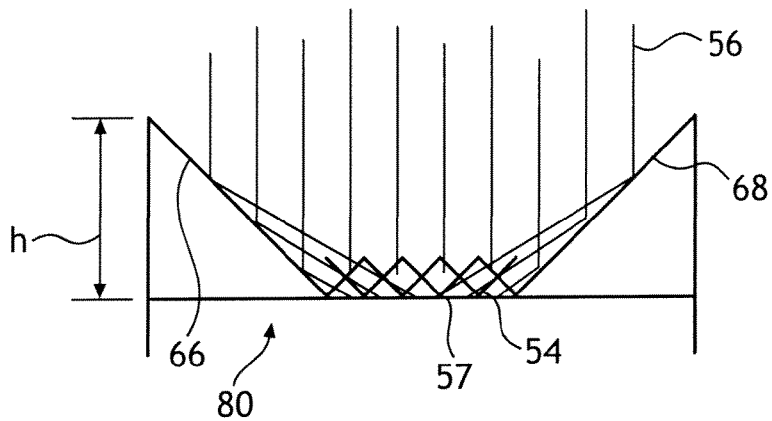
FIGS. 9A and 9B are illustration of representative cross section of the apparatus of FIG. 8.
Figure 9B:
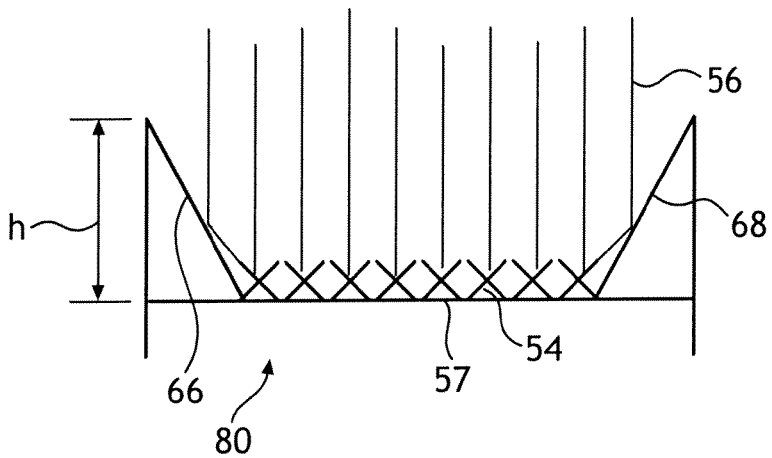

FIGS. 9A and 9B show cross sectional view of the apparatus of FIG. 8 illustrating one specific design and a composite stream 56. Specifically FIG. 9A illustrates a cross sectional view of the apparatus of FIG. 8 as viewed along line A-A where the composite stream 56 is collected on the collection surface 57 at a minimum width. FIG. 9B illustrates a cross sectional view of the apparatus of FIG. 8 as viewed along line B-B where the composite stream 56 is collected on the collection surface 57 at a maximum width. As illustrated in FIGS. 9A and 9B the deflectors 66, 68 have a constant height h, the amount of the collection surface 57 exposed to the composite stream 56 being determine by the angle that the deflectors 66, 68 intersect the composite stream 56.

Figure 9C:
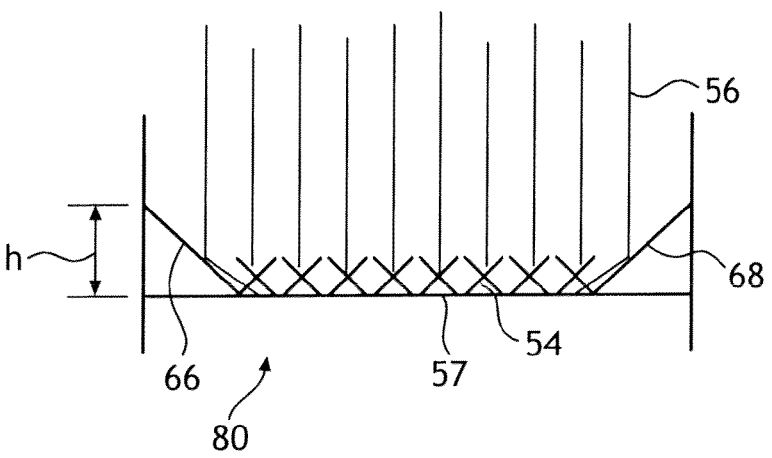
FIG. 9C is an illustration of an alternative cross section of an apparatus like that of FIG. 8.

FIG. 9C illustrates a second design of deflectors 66, 68 to achieve a collection surface 57 with varying width. Specifically, instead of changing the angle that the deflectors 66, 68 intersect the composite stream 56, the angle remains constant and the height h is adjusted to vary the width of the collection surface 57 that is exposed to the composite stream 56.

It will be appreciated that details of the apparatus and methods of the invention, given for purposes of illustration, are not to be construed as limiting the scope of this invention. Although only a few exemplary aspects of this invention have been described in detail above, those skilled in the art will readily appreciate that many modifications are possible in the exemplary aspects without materially departing from the novel teachings and advantages of this invention. Accordingly, all such modifications are intended to be included within the scope of this invention, which is defined in the following claims and all equivalents thereto. Further, it is recognized that many aspects may be conceived that do not achieve all of the advantages of some aspects, particularly of the preferred aspects, yet the absence of a particular advantage should not be construed to necessarily mean that such an aspect is outside the scope of the present invention.

The invention claimed is:

1. A method for forming a shaped fibrous nonwoven structure, comprising:
    delivering a high speed composite stream comprising thermoplastic polymer fibers and a secondary material;
    mechanically redirecting at least a portion of the composite stream with a deflector;
    collecting the composite stream on a collection surface of a movable collection device;
    wherein the deflector moves in synchronization with the movable collection device, such that the composite stream is collected on the collection surface forming a fibrous nonwoven structure having at least one non-linear edge.

2. The method of claim 1 wherein the high speed composite stream is delivered at a velocity of at least 50 feet/second (15 m/sec).

3. The method of claim 1 wherein the high speed composite stream comprises from about 1-50% by weight absorbent fibers, from about 30-99% superabsorbent particles and about 5-90% polymer fibers.

4. The method of claim 3 wherein the absorbent fibers are cellulose fibers and the thermoplastic polymer fibers are elastic fibers.

5. The method of claim 1 wherein the movable collection device is an endless belt.

6. The method of claim 1 wherein the movable collection device is a porous rotating drum.

7. The method of claim 1 wherein the high speed composite stream contains absorbent fibers.

8. The method of claim 1 wherein the high speed composite stream contains superabsorbent particles.

9. The method of claim 1 comprising a first deflector and a second deflector, wherein the first deflector mechanically redirect at least a first portion of the composite stream, the second deflector mechanically redirect at least a second portion of the composite stream.

10. The method of claim 9, wherein the first deflector and the second deflector are slidably attached to the movable collection device.

11. The method of claim 1 wherein the deflector rotates about an axis.

12. The method of claim 11 wherein the axis is substantially parallel to the composite stream.

13. The method of claim 11 wherein the axis is substantially perpendicular to the composite stream.

14. The method of claim 1 wherein the deflector intersects the high speed composite stream at an angle of not greater than 40 degrees.

15. A method for forming a shaped fibrous nonwoven structure, comprising:

delivering a high speed composite stream comprising thermoplastic polymer fibers and a secondary material at a velocity of at least 50 feet/second (15 m/sec);

mechanically redirecting at least a portion of the composite stream with a deflector;

collecting the composite stream on a collection surface of a movable collection device;

wherein the deflector is fixedly attached to the movable collection device, such that the composite stream is collected on the collection surface forming a fibrous nonwoven structure having at least one non-linear edge, and the high speed composite stream comprises from about 5-25% by weight cellulose fibers, from about 40-90% superabsorbent particles and about 5-55% thermoplastic polymer fibers.

16. The method of claim 15 wherein the movable collection device is an endless belt.

17. The method of claim 15 wherein the movable collection device is a porous rotating drum.

18. The method of claim 15 wherein the high speed composite stream contains absorbent fibers.

19. The method of claim 15 wherein the high speed composite stream contains superabsorbent particles.

20. The method of claim 15 wherein the at least one deflector intersects the high speed composite stream at an angle of not greater than 40 degrees.

* * * * *